(12) United States Patent
Jones

(10) Patent No.: US 7,052,720 B1
(45) Date of Patent: May 30, 2006

(54) SPHEROID PREPARATION

(75) Inventor: Derek Leigh Jones, Cardiff (GB)

(73) Assignee: University of Wales College of Medicine, Cardiff (GB)

( * ) Notice: Subject to any disclaimer, the term of this patent is extended or adjusted under 35 U.S.C. 154(b) by 505 days.

(21) Appl. No.: 10/009,765

(22) PCT Filed: Jun. 19, 2000

(86) PCT No.: PCT/GB00/02215

§ 371 (c)(1),
(2), (4) Date: Dec. 17, 2001

(87) PCT Pub. No.: WO00/78927

PCT Pub. Date: Dec. 28, 2000

(30) Foreign Application Priority Data

Jun. 17, 1999 (GB) .................................. 9913979

(51) Int. Cl.
*A61K 35/16* (2006.01)
(52) U.S. Cl. .................................................. 424/531
(58) Field of Classification Search ................ 424/531
See application file for complete search history.

(56) References Cited

U.S. PATENT DOCUMENTS

| 4,237,033 | A | 12/1980 | Scattergood |
| 5,601,845 | A | 2/1997 | Buxton et al. |
| 5,624,839 | A | 4/1997 | Yada et al. |
| 5,643,787 | A | 7/1997 | Barsky et al. |

FOREIGN PATENT DOCUMENTS

| EP | 0 529 659 A2 | 3/1993 |
| JP | A 5-260957 | 10/1993 |
| JP | A 6-339367 | 12/1994 |
| JP | A 7-79772 | 3/1995 |
| JP | A 8-70847 | 3/1996 |
| JP | A 9-140377 | 6/1997 |
| JP | A 10-29951 | 2/1998 |
| JP | A 11-180878 | 7/1999 |

OTHER PUBLICATIONS

Blaauboer et al., Biochemical and Biophysical Research Communications 90(1): 368-374 (Sep. 12, 1979).*
XP-000971592, Murakami et al., "*Formation of Ovary-Like Multitissue Spheroids Composed of Isolated Rat Follicles in Vitro*", Journal of Reproduction and Development, vol. 39, No. 4, 1999.
Toshiaki Takezawa et al., "Morphological and Immuno-Cytochemical Characterization of a Hetero-Spheroid Composed of Fibroblasts and Hepatocytes," Journal of Cell Science, V. 101, 1992, pp. 495-501.
John M. Yuhas et al., "A Simplified Method for Production and Growth of Multicellular Tumor Spheroids," Cancer Research, V. 37, 1977, pp. 3639-3643.
Robert M. Sutherland et al., "Growth of Multicell Spheroids in Tissue Culture as a Model of Nodular Carcinomas," Journal of the National Cancer Institute, V. 46, 1971, pp. 113-120.
Norio Koide et al., "Formation of Multicellular Spheroids Composed of Adult Rat Hepatocytes in Dishes with Positively Charged Surfaces and under other Nonadherent Environments," Experimental Cell Research, V. 186, 1990, pp. 227-235.
M. Kamihira et al., "Spheroid Formation of Hepatocytes Using Synthetic Polymer," Ann N Y Acad Sci, V. 831, 1997, pp. 398-407, (Abstract).
Toshiaki Takezawa et al., "Cell Culture on a Thermo-Responsive Polymer Surface," Bio/Technology, V. 8, 1990, pp. 854-856.
Toshiaki Takezawa et al., "Characterization of Morphology and Cellular Metabolism During the Spheroid Formation by Fibroblasts," Experimental Cell Research, V. 208, 1993, pp. 430-441.

* cited by examiner

*Primary Examiner*—Jean C. Witz
(74) *Attorney, Agent, or Firm*—Young & Thompson

(57) ABSTRACT

A mixture or substance having a spheroid-forming activity is obtained by heat treating fetal calf serum at a temperature and for a period sufficient to impart spheroid-forming activity. Introduced into cell culture, the substance or mixture so obtained causes cells to grow in three-dimensional cultures as opposed to mono-layer. Also disclosed are kits for the production of said mixture or substance and further uses of said mixture or substance.

32 Claims, 3 Drawing Sheets

PARALLEL JOINED STRING SPHEROIDS IN THE FORM OF A GRID (FORMED IN A GRID 'V' CHANNEL VESSEL WHERE THE BOTTOM OF THE 'V' CHANNELS ARE SPACED 1cm APART)

SPHEROID PREPARATION

This invention relates to a method of producing a substance or mixture having spheroid-forming activity from fetal calf serum and to methods of spheroid formation.

Spheroids are three-dimensional cultures of cells which are normally grown in suspension. A number of processes for formation of spheroids have been proposed, for example in U.S. Pat. No. 5,624,839, but these have been found to be relatively complex. Although the term "spheroid" is often used conventionally to describe an object of approximately spherical shape, the term is used more broadly herein to describe any three-dimensional cell structure in which the cells are grown in suspension as opposed to in a mono-layer on a substrate. Thus the term spheroid embraces not only approximately spherical clusters of cells, but also string-like structures or lattice or net-like structures in which the cells form a three dimensional structure not of mono-layer form.

Spheroids in general are used in tissue culture research, for example.

According to the first aspect of the present invention, there is provided a method of producing a substance or mixture for use in spheroid formation, the method comprising heat treatment of fetal calf serum for a time and at a temperature sufficient to impart spheroid-forming activity to the resultant substance or mixture.

The heat treatment is preferably performed at a temperature between 60° C. and 80° C., even more preferably between 65° C. and 75° C. However, it is envisaged that temperatures outside these ranges could be used, particularly below these ranges, although in such a case the incubation time would be longer. The heat treatment, for example, may be performed for between 30 minutes and 12 hours. It has been found that, for many batches of FCS, the optimum conditions for producing the substance or mixture are 70° C. for 5 hours. However, different amounts of the substance or mixture may be produced at different temperatures and incubation times, with generally more being produced at the higher temperature and longer incubation time. Nevertheless, higher temperatures may give rise to too much coagulation of proteins in the serum, thus resulting in a loss of activity in the substance or mixture.

The method may further comprise the step of storing the resultant substance or mixture in aliquots at about –20° C.

According to a second aspect of the present invention, there is provided a substance or mixture for use in spheroid preparation formed by the method described above.

According to a further aspect of the present invention, there is provided a method of forming a spheroid comprising contacting in a vessel a cell culture with a substance or mixture formed by the method described above.

One or more cell types may be used, thus enabling the method to be used in the formation of heterospheroids in addition to homospheroids. Indeed, heterospheroids may be easily formed by adding several cell types in the required ratio.

The method of spheroid formation typically requires an overnight incubation period.

Spheroid size can be regulated by initial cell number, time of incubation and shape of culture vessel. Generally, small and medium sized spheroids (up to 100 micrometres), are formed after 24 hours and their size is increased thereafter mainly by fusion of spheroids rather than by cell growth.

The substance or mixture for use in spheroid preparation may, in one embodiment be coated on to the vessel, which may be formed of plastic. Alternatively, spheroid preparation may be carried out on uncoated vessels and, in such a case, a 5 to 10% solution of the substance or mixture for use in spheroid preparation may be added to a medium of the cell culture.

According to a further aspect of the present invention, there is provided an elongate spheroid comprising a plurality of cells arranged linearly.

The elongate spheroids are known as "string spheroids". Typically, the elongate spheroid may have a length of at least about 1 cm, or preferably about 2 cm. Typically, it has been found that elongate spheroids may be of the order of 0.2–0.5 mm in diameter and may typically be 25 cm long, containing 100,000–150,000 cells per cm length. However, it should be noted that elongate spheroids may be of 100 cm in length or even more.

Again, the cells may be of one or more types, thus producing two homo- or hetero-string spheroids. In one example, MCF7 and breast fibroblast cell lines have been prepared. One or more layers may be arranged around an inner elongate arrangement of cells. ECV cells have additionally been used to provide three cell layers in a triple string spheroid.

According to a further aspect of the present invention, there is provided a method of forming an elongate spheroid comprising forming a suspension by contacting a cell culture with a spheroid-forming substance or mixture formed by the method described above at the required concentration, placing the suspension in a tubular member, incubating the contents of the tubular member, and removing the elongate spheroid. Typically, the required concentration is in the range of 6 to 10 million cells per milliliter. In one embodiment, the tubular member may have an internal diameter of about 1 mm. Typically, the tubular member may be in the form of a "butterfly" having a length of about 25 cm and an outer diameter of 2 mm, but any appropriate tubing, for example one of plastic and of suitable dimensions, could be used.

The method may further comprise the step of stretching the tubular member prior to incubation, and preferably holding the tube in a horizontal position.

According to a further aspect of the present invention, there is provided a kit for forming elongate spheroids, comprising a substance or mixture for use in spheroid formation formed by the method described above, and a culture vessel. The culture vessel may be tubular or of one or more elongate components side by side or in a grid or lattice formation and having a v-sectioned base.

The kit may further comprise the cells which it is desired to form into an elongate spheroid, means for placing a suspension into the tubular member, means for removing the elongate spheroid from the tubular member and/or a stand for arranging the tubular member horizontally during incubation.

Many uses for the substance or mixture for use in spheroid formation according to this invention can be envisaged and examples include the following:

(i) It could be easily prepared as a commercially available product, either in its crude form or a purified form, for the production of homo- or heterospheroids in tissue culture research.

(ii) It could be used for the preparation of string spheroids made of different cell types such as fibroblasts, smooth muscle cells, and endothelial cells to make in-vitro veins.

(iii) It could be used for the preparation of keratinocyte/fibroblast and other skin cell mini-spheroids that could be attached to an artificial support for use as a sort of skin grafting. This could produce micro-islands of skin cells on the surface of open large area wounds. The closeness of the spheroids could be controlled to give optimum outgrowth and link up of skin islands, whilst initially allowing wound exuate etc. to pass between the islands.

(iv) It could form the basis for another angle on anti-cancer therapy. When tumour cells are cultured as spheroids with the substance or mixture of the invention, their growth is slowed right down, and the cells stick together much more strongly (hence spheroid formation). It could therefore form the basis for an anti-metastatic factor and/or an agent to slow down or even stop tumour cell growth.

Thus, according to a further aspect of the present invention, there is provided the use of a substance or mixture for use in spheroid formation formed by the method described above in anti-cancer therapy.

The invention also extends to a polymer material comprising a polymer of one or more proteins contained in fetal calf serum, having a molecular weight of at least 2 MDa and a spheroid forming activity.

In another aspect this invention provides a polymeric protein comprising a polymer of one or more proteins contained in fetal calf serum, having a molecular weight in excess of 2 MDa and having spheroid forming activity.

In another aspect this invention provides a polymeric protein obtainable by heat treatment of fetal calf serum, whereby said polymeric protein is capable of spheroid forming activity.

In another aspect this invention provides the use of a polymeric protein for the preparation of skin cells selected from the group comprising keratinocytes and fibroblasts, for use in wound healing and/or skin grafting.

In another aspect this invention provides a method of elongate spheroid formation, which comprises providing an elongate culture vessel having a generally V-shaped lower cross-section, introducing into said culture vessel a cell culture and a spheroid-forming substance or mixture, incubating the contents of said vessel and removing the elongate spheroid.

For convenience, in the description below, "Spefadel" is the name given to the spheroid forming substance or mixture of the present invention produced by heat treatment of commercially available fetal calf serum (FCS).

Although the invention has been defined above, it is to be understood that it includes any inventive combination of the features set out above or in the following description.

The invention may be performed in various ways, and specific examples will now be described, by way of example, with reference to the accompanying drawings, in which.

EXAMPLE 1

Preparation of "Spefadel"

Figure 1:
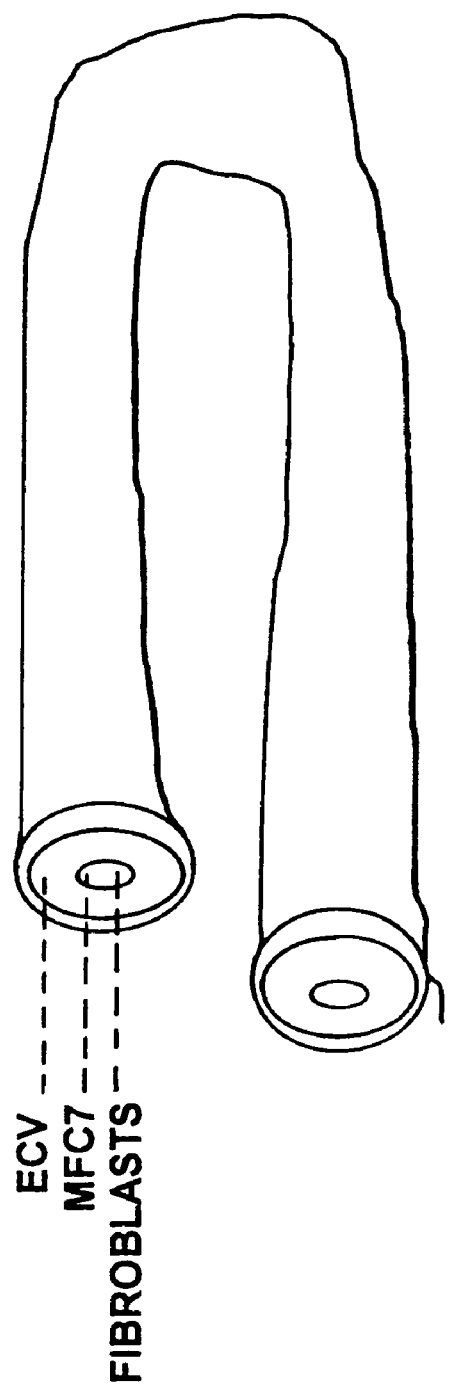
FIG. 1 is a diagrammatic view, partially in cross section, of a triple string spheroid formed in accordance with the invention.

Heat treatment of Fetal Calf Serum (FCS) in a waterbath at a temperature of between 65 and 75° C. for 30 mins to 7 hours gives rise to the substance or mixture known as 'Spefadel'. Different amounts of 'Spefadel' are produced at different temperatures and incubation times, with more 'Spefadel' being produced at the higher temperature and longer incubation time. The optimum conditions for the production of 'Spefadel' are 70° C. for 5 hours. Higher temperatures, that is 75° C. or above, give rise to too much coagulation of proteins in the serum, resulting in loss of 'Spefadel' activity.

No spheroid forming activity was found in FCS heat treated at 60° C. for up to 4 hours, but there was 'Spefadel' activity after 7 hours incubation at this temperature.

It should be noted that the production and amount of 'Spefadel' may vary according to different batches of FCS. In this instance the temperature and length of treatment may be adjusted and the spheroid forming activity of the 'Spefadel' tested.

'Spefadel' is typically prepared by heating FCS at 70° C. for 5 hours and storing in aliquots at −20° C. until required.

EXAMPLE 2

Spheroid Preparation with Spefadel

Spheroids can be prepared from different cell lines in ordinary sterile tissue culture flasks/petri dishes or sterile non-tissue culture flasks/petri dishes. Spheroids can be prepared in flasks/dishes that have been pre-coated with 'Spefadel' for 24 hrs or longer and then washed to remove any proteins etc. that have not adsorbed to the surface. Spheroids can be prepared in flasks/dishes in the presence of 1% to 10% 'Spefadel' in any standard tissue culture medium e.g. RPMI1640, DMEM, DMEM/F12 etc. Spheroids are only formed by cells in suspension and not by cells already attached to plastic tissue culture vessels. If 10% 'Spefadel' medium is added to subconfluent monolayers of all cell types tested, they continue to grow as monolayers and grow at almost the same rate as cells cultured with FCS supplemented medium. 'Spefadel' under these conditions is completely non-toxic to the cells.

Spheroid Preparation on Coated Plastic Vessels

The vessel to be used for the preparation of spheroids can be of virtually any type of non-toxic plastic suitable for cell culture, but must be sterile. Typical vessels used successfully have included Nunc/Sterilin 25 $cm^2$ tissue culture flasks, Sterilin 90 mm bacteriological plates, Falcon 25 mm and 50 mm tissue culture plates, and 96, 24 and 6 well Nunc microtest plates.

'Spefadel' at about 1 ml/15 sq cm of plastic surface was added and spread evenly over its surface. The vessel was then placed in a 37° C. incubator for between 24 and 72 hours. After the required time the 'Spefadel' was removed and the surface of the vessel was given 3×10 min washes with 5 ml aliquots of serum free medium (such as DMEM/F12) before adding about 4 ml of the same medium containing 1 mg/ml Bovine Serum Albumin (BSA), penicillin (100 units/ml), streptomycin (100 µg/ml) and fungizone (2 µg/ml) (these three antibiotics together at these concentrations are known as PSF).

Breast tumour cell lines such as MCF7, MDA231 and BT474, human fibroblasts from breast and skin and a bladder cancer cell line such as ECV all available from ECACC or ATCC have all been used to prepare spheroids on coated plastic vessels. Basically cells were cultured as monolayers in a standard fashion in 25 cm$^2$ Nunc tissue culture flasks with DMEM/F12 containing 10% FCS and PSF in a 37° C. incubator with 5% $CO_2$, until almost confluent when they were made into a cell suspension with trypsin/EDTA (0.05% porcine trypsin and 0.05% EDTA in phosphate buffered saline). Cells were made up in complete 10% FCS medium and counted before centrifugation at 400G and resuspension at 1 million cells/ml in SFM with PSF and BSA. For homospheroids about 1 ml of the cell suspension was added to each 25 cm$^2$ flask and left in the $CO_2$ incubator for 24 hrs, after which time spheroids were formed as clusters of 20 to hundreds or even thousands of cells. Initially small spheroids were formed by attachment of cells to each other and then larger spheroids were formed by the fusion of small spheroids. Generally speaking spheroid size can be modulated by the number of cells used and the length of time they are left together. Increasing either incubation time or cell number usually gives an increase in the size of spheroids.

Heterospheroids with different ratios of cells can easily be prepared. For example the addition of 250 000 fibroblast cells to 1 million MCF7 cells gives rise to spheroids with 4 times as many MCF7 cells as fibroblasts. The fibroblasts always end up at the centre of the heterospheroid surrounded by MCF7 cells, regardless of cell number ratios or even if the fibroblasts are added to MCF7 cells that have already formed spheroids.

Spheroid Preparation on Uncoated Plastic Vessels

The culture vessels and basic medium to be used for the preparation of spheroids on uncoated plastic are exactly the same as those used for the coated method. The main differences in the method is the addition of 5 to 10% 'Spefadel' to the basic culture medium instead of 1 mg/ml BSA. All other conditions used for the preparation of spheroids on coated plastic apply to the preparation of spheroids on uncoated plastic.

EXAMPLE 3

String Spheroid Preparation

String spheroids are made from cells prepared in suspension in 10% 'Spefadel', similar to those for spheroids on uncoated plastic. In order for cells to form a complete string they have to be seeded at a certain concentration so that there are enough cells present to form a complete string but not too many cells present so as to use up all the nutrients and give rise to excessive cell death.

Actual cell numbers used for string spheroids also depend on the cell type used and some cells such as fibroblasts only form short lengths of string spheroid, probably due to weaker connections between the cells, when compared to cells of epithelial type such as MCF7 or BT474 tumour cell lines.

Cells are prepared in suspension in 10% 'Spefadel' medium as previously described. For most cell types the optimum cell number for string spheroid preparation is between 6 and 10 million cells/ml. For MCF7 and BT474 cells the optimum is about 8 million cells/ml. Once the cells are prepared in suspension at the required concentration they are ready to be placed in a disposable sterile string spheroid apparatus. The apparatus currently used is very simple and consists of a sterile 21 gauge "butterfly" (Registered Trade Mark) with a tube length of about 25 cms of internal/external diameter about 1 mm and 2 mm respectively. The "butterfly" is a hollow needle connected to a luer syringe connector by a hollow plastic tube. Other sizes may be used.

The method for string spheroid preparation of MCF7 cells will now be described.

Prepare a suspension of 8 million MCF7 cells/ml in 10% 'Spefadel' as already described. Take a 1 ml disposable syringe and suck up 0.65 ml of 10% 'Spefadel' medium and then, taking care not to get any air bubbles, suck up slowly 0.35 ml of the MCF7 cell suspension, whilst holding the syringe vertical, so that it forms a separate layer in the syringe. Connect the syringe to the butterfly and slowly press the syringe whilst still holding vertical until the suspension reaches the end of the plastic butterfly tube (care must be taken to avoid the introduction of air bubbles, as these will cause breaks in the string spheroid) which will be about 0.35 ml in volume. Immediately slightly stretch the tubing over a horizontal holding frame so that the tube is held in a straight line in a horizontal position. Several string spheroids are usually made at any time and the current holding frame can accommodate up to 6 tubes. The whole process is done aseptically in a laminar flow hood to minimise contamination by microorganisms. The frame and tubes are now placed in a 5% $CO_2$ incubator and left overnight (18 hours). After this time the tubes are removed singly and cleaned with a steriswab before cutting the plastic tube aseptically close to the needle end of the butterfly. The tube contents are then ejected slowly (by gently pressing the syringe to push the remaining 0.7 ml of medium through the tube) into 10 ml of 1% 'Spefadel' medium in a 90 mm sterile plastic plate. The result is a 'string spheroid' of MCF7 cells about 20 cm long containing about 150,000 cells per cm length.

Hetero-string spheroids containing 2 and 3 cell types have also been prepared using the same method. Heterospheroids containing MCF7 and breast fibroblast cell lines have been prepared using cell suspensions containing 6 million MCF7 and 3 million fibroblasts per ml of medium. In this hetero-string spheroid the fibroblasts are always at the centre surrounded by MCF7 cells. In the triple string spheroid ECV cells were also present in the cell suspension and these formed a layer of cells around the MCF7 cells to give three cell layers as shown in FIG. 1.

Figure 2:
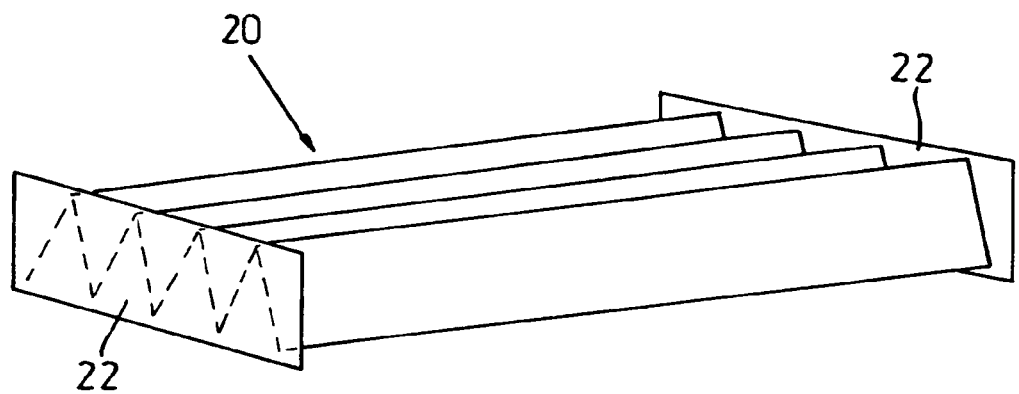
FIG. 2 is a schematic perspective view of a culture vessel comprising a plurality of v-channels for string spheroid preparation.
Figure 3:
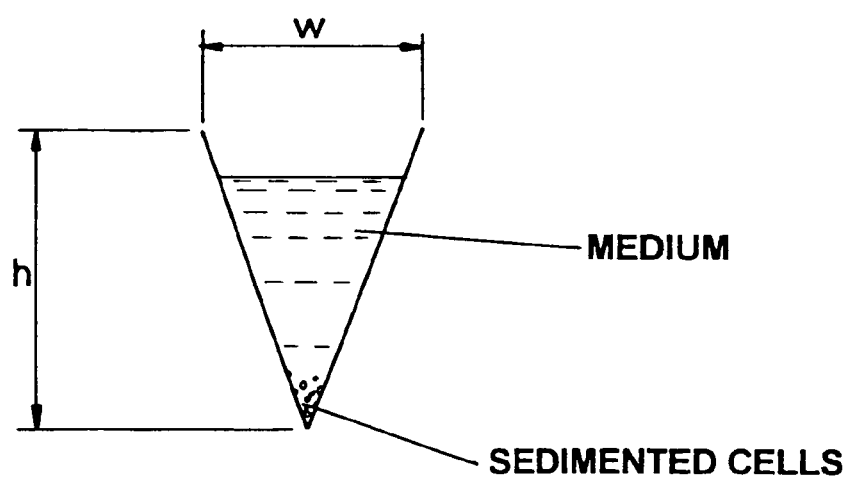
FIG. 3 is a cross-section of one of the v-channels showing the sedimented cells.

Referring now to FIGS. 2 and 3, an alternative method of preparation of string spheroids will now be described.

EXAMPLE 4

In this method string spheroids are prepared using cells suspended in 10% Spefadel in DMEM/F12 medium. It requires the use of a special shaped culture vessel 20 made out of polystyrene, polycarbonate or any material compatible with cell culture and which has a v-shaped corrugated profile as seen in FIGS. 2 and 3. The dimensions for the 'V' profile used may vary from between 5 mm and 15 mm wide (w) and 5 mm and 15 mm tall (h). The length of the 'V' channel used may typically be up to 15 cm but longer lengths can be used. Just one V-profile may be used, but usually several 'V' profiles are joined to each other giving rise to a vessel containing a series of parallel 'V' channels. The ends of the 'V' channel are blocked off by walls 22.

In this method a cell suspension in 10% Spefadel DMEM/F12 medium is placed in the 'V' channel which is then placed on a level surface in an incubator. The cells fall through the liquid due to gravity, and because the sides of the channel are sloped nearly all the cells fall to the bottom groove of the channel to give a continuous length of sedimented cells as seen in FIG. 3.

After 24 to 36 hours the cells attach to each other to give a string spheroid which can be gently removed from the 'V' channel or left in situ where the medium can be carefully changed when required. Homo and hetero-string spheroids can be prepared by this method using one cell type or mixed cell type cell suspension.

Cell concentrations used for this method vary depending on the cell type and the volume of liquid placed in the 'V' channel. Generally cell concentrations are adjusted so that when the cells are sedimented there are about 100000 to 200000 cells for each centimeter in length of the channel. Thus a 'V' channel of 15 cm length containing 5 ml of medium might typically require a cell concentration of 0.3 to 0.6 million cells/ml.

EXAMPLE 5

Figure 4:
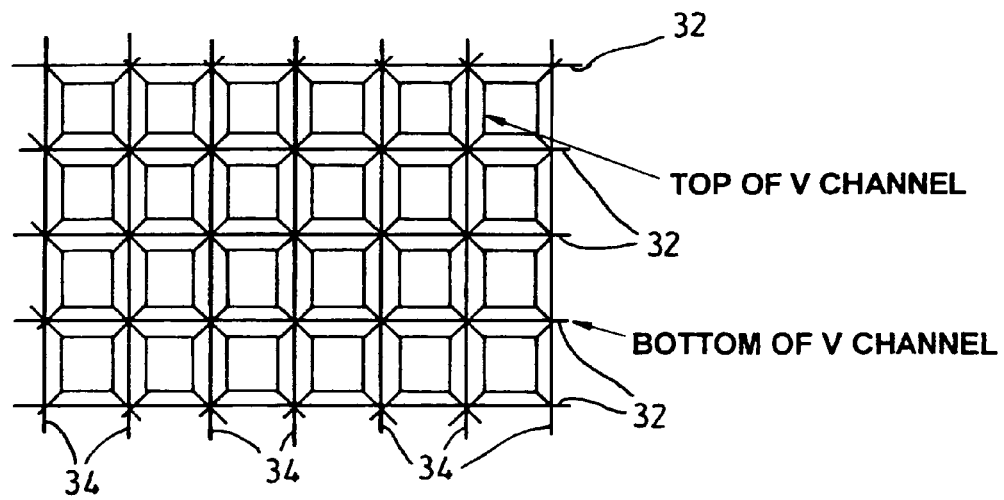
FIG. 4 is a schematic top plan view of a culture vessel comprising a grid of v-channels, for spheroid preparation.
Figure 5:
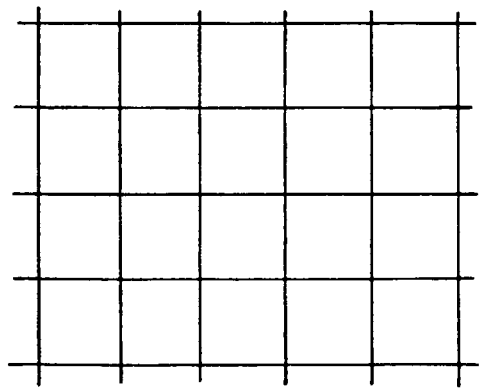
FIG. 5 is a schematic view of a grid string spheroid produced in the vessel of FIG. 4.

This is another variation of the 'V' channel method. Referring now to FIGS. 4 and 5, the main modification is the 'V' channel vessel 30 in which the cells are sedimented. It consists of two sets of 'V' channels (32, 34) at right angles to each other so that a grid of interconnected 'V' channels is formed. Dimension of the 'V' channel cross section, cell suspensions and incubation conditions used may be the same as those for the linear 'V' channel method of Example 4. When cells are placed in the 'V' channel grid they sediment and form string spheroids at right angles to each other which are joined where their paths cross. This results in the formation of a 'Grid string spheroid' (FIG. 5), the dimensions of which depend on the spacing between the 'V' channels in the vessel.

A possible advantage of the 'V' channel methods of Examples 4 and 5 over the tube method for string spheroid preparation is that after string spheroid formation by a first cell type one could remove the medium and add a cell suspension of a second cell type. This would allow the sequential addition of different cell types giving rise to another method for hetero-string spheroid preparation.

List of Abbreviations

| abbreviation | description |
|---|---|
| BSA | Bovine serum albumin |
| BT474 | Breast tumour cell line |
| CO2 | Carbon dioxide |
| DMEM | Dulbeccos Minimal Essential Medium |
| DMEM/F12 | Dulbeccos Minimal Essential Medium/Hams F12 tissue culture medium |
| ECV | Bladder Cancer cell line |
| EDTA | Ethylenediaminetetraacetic acid |
| FCS | Fetal Calf Serum |
| MCF7 | Breast tumour cell line |
| PFS | penicillin (100 u/ml), fungizone (2 µg/ml) and streptomycin (100 µg/ml) |
| RPMI1640 | Roswell Park Memorial Institute 1640 tissue culture medium |

The invention claimed is:

1. A method of producing a substance or mixture for use in spheroid formation, the method comprising heat treatment of Fetal Calf Serum for a time and at a temperature sufficient to impart spheroid-forming activity to the resultant substance or mixture wherein the heat treatment is performed at a temperature between 60° C. and 80° C. for between 30 minutes and 12 hours.

2. The method according to claim 1, wherein the heat treatment is performed at a temperature between 65° C. and 75° C.

3. The method according to claim 1, wherein the heat treatment is performed at a temperature of 70° C. for about five hours.

4. The method according to claim 1, further comprising the step of storing the resultant substance or mixture in aliquots at about −20° C.

5. A substance or mixture for use in spheroid preparation formed by the method according to claim 1.

6. A method of spheroid formation comprising contacting in a vessel a cell culture with a substance or mixture formed by the method of claim 1.

7. The method according to claim 6, wherein the spheroid-forming substance or mixture is coated on the vessel.

8. The method according to claim 6, wherein a 5 to 10% solution of the spheroid-forming substance or mixture is added to a medium of the cell culture.

9. The method according to claim 6, wherein the cell culture comprises more than one cell type, whereby a hetero-spheroid is formed.

10. An elongate spheroid, produced by a method according to claim 6, said elongate spheroid comprising a plurality of cells arranged linearly.

11. The elongate spheroid according to claim 10 which has a length of at least 1 cm.

12. The elongate spheroid according to claim 10, which contains 100,000–200,000 cells per cm length.

13. The elongate spheroid according to claim 10, comprising more than one cell type.

14. The elongate hetero-spheroid according to claim 10, comprising an elongate core of cells of one type with one or more layers of cells of a different type arranged around said core.

15. An elongate hetero-spheroid produced by a method according to claim 6, wherein said hetero-spheroid comprises MCF7 and breast fibroblast cells.

16. A method of forming an elongate spheroid comprising forming a suspension by contacting a cell culture with a spheroid-forming substance or mixture according to claim 1 at the required concentration, placing the suspension in a tubular member, incubating the contents of the tubular member, and removing the elongate spheroid.

17. The method according to claim 16, wherein the required concentration is in the range of 6 to 10 million cells/ml.

18. The method according to claim 16, wherein the tubular member has an internal diameter of about 1 mm.

19. The method according to claim 16, further comprising the step of stretching the tubular member prior to the incubation.

20. A kit for forming elongate spheroids comprising a spheroid forming substance or mixture according to claim 5 and a tubular member.

21. A method for producing a spheroid of cancer cells, comprising adding to a culture of cancer cells an effective amount of a spheroid-forming substance or mixture formed by the method of claim 1.

22. A polymeric protein comprising a polymer of one or more proteins contained in fetal calf serum, having a molecular weight in excess of 2 MDa and having spheroid forming activity, wherein said polymeric protein is produced by heat treatment of fetal calf serum for a time and at a temperature sufficient to impart a spheroid-forming activity and wherein the heat treatment is performed at a temperature between 60° C. and 80° C. for between 30 minutes and 12 hours.

23. A polymeric protein produced by the method according to claim 1, whereby said polymeric protein is capable of spheroid forming activity.

24. A method for the production of spheroids for tissue culture comprising adding an effective amount of a polymeric protein according to claim 22 to a culture of tissue cells.

25. A method for the production of spheroids made up of one or more of fibroblasts, smooth muscle cells and bladder cancer cells, comprising adding to a culture of fibroblasts, smooth muscle cells, bladder cancer cells an effective amount of a protein according to claim 22.

26. A method for the preparation of skin cells selected from the group comprising keratinocytes and fibroblasts, comprising adding to a culture of keratinocytes and fibroblasts an effective amount of a polymeric protein according to claim 22.

27. A method of elongate spheroid formation, comprising providing an elongate culture vessel having a generally V-shaped lower cross-section, introducing into said culture vessel a cell culture and a spheroid-forming substance or mixture according to claim 5, incubating the contents of said vessel and removing the elongate spheroid.

28. A method of producing a spheroid making up a grid structure, which comprises providing a corresponding culture vessel defining a grid in which the grid elements are of V-section, and introducing into said culture vessel a cell culture and a spheroid-forming substance or mixture according to claim 5, incubating the contents of said vessel and removing a spheroid of grid-like structure.

29. The method according to claim 27, wherein said incubation is for a period of 24 to 36 hours.

30. The method according to claim 27, wherein said V-shaped section defines an inclined angle in the range of from 200 to 120°.

31. A kit for forming elongate spheroids or a grid-like structure thereof, comprising a culture vessel having an elongate portion with a generally V-shaped lower cross-section, and a spheroid-forming substance or mixture according to claim 5.

32. A method of spheroid formation comprising contacting in a vessel one or more cell cultures with a polymeric protein according to claim 22.

* * * * *